United States Patent [19]
Platz et al.

[11] 3,988,379
[45] Oct. 26, 1976

[54] MANUFACTURE OF CYCLOHEXANOL FROM CYCLOHEXENE

[75] Inventors: Rolf Platz, Mannheim; Werner Fuchs; Christian Dudeck, both of Ludwigshafen, all of Germany

[73] Assignee: Badische Anilin- & Soda-Fabrik Aktiengesellschaft, Ludwigshafen (Rhine), Germany

[22] Filed: July 5, 1974

[21] Appl. No.: 486,058

Related U.S. Application Data
[63] Continuation of Ser. No. 252,831, May 12, 1972, abandoned.

[30] Foreign Application Priority Data
May 18, 1971  Germany............................ 2124590

[52] U.S. Cl............................................ 260/631 R
[51] Int. Cl.²......................................... C07C 29/06
[58] Field of Search................... 260/631 H, 631 R

[56] References Cited
UNITED STATES PATENTS
| | | | |
|---|---|---|---|
| 1,948,891 | 2/1934 | Van Peski | 260/153 |
| 2,414,646 | 1/1947 | Hepp | 260/631 |

*Primary Examiner*—James O. Thomas, Jr.
*Assistant Examiner*—James H. Reamer
*Attorney, Agent, or Firm*—Johnston, Keil, Thompson & Shurtleff

[57] ABSTRACT

A continuous process for the manufacture of cyclohexanol from cyclohexene in two stages involving the addition of sulfuric acid and hydration, the addition of sulfuric acid being carried out in the presence of iron-(II) sulfate. In a special embodiment, the addition of sulfuric acid is carried out in the first stage at atmospheric pressure and at the boiling temperature of cyclohexene.

3 Claims, 1 Drawing Figure

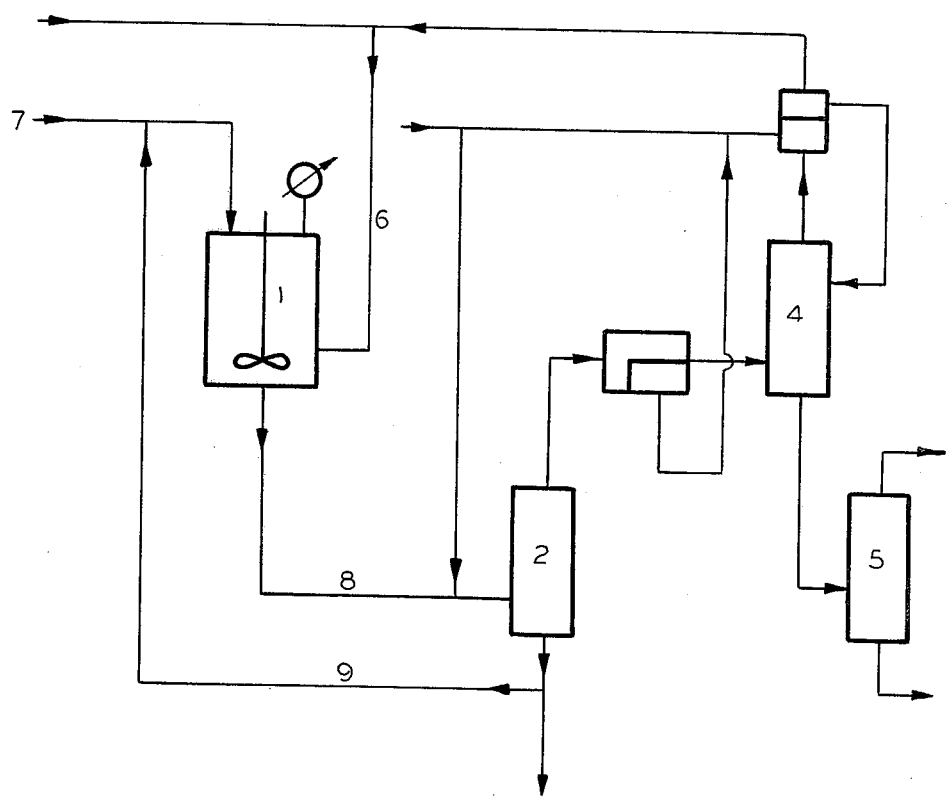

MANUFACTURE OF CYCLOHEXANOL FROM CYCLOHEXENE

This is a continuation of application Ser. No. 252,831, filed May 12, 1972, now abandoned.

It is known to produce alcohols from olefins by hydration. The method may be carried out in two ways. The first way of hydrating olefins to alcohols resides in the direct catalytic addition of water to the olefinic double bond. This may be carried out by passing the olefin together with steam at high temperatures and pressures over suitable catalysts, for example "solid" phosphoric acid, as may be obtained by applying phosphoric acid to silica gel, activated charcoal or asbestos. This procedure is only suitable for olefins which are stable under these conditions and is substantially limited to lower olefins. The process of direct catalytic hydration is an equilbrium process. In a single pass of the reactants through the reactor, only a few percent of the olefin is converted to alcohol and it is therefore necessary to recycle the unreacted portion.

The other way of hydrating olefins is to convert the olefins to the corresponding alkyl sulfuric acid or alkyl sulfate with sulfuric acid and, in a second stage, to hydrolyze said alkyl compounds to alcohol and sulfuric acid. The sulfuric acid is concentrated and returned to the process.

It is also known to produce cyclohexanol by hydrating cyclohexene with 80% sulfuric acid, which process is carried out in the presence of catalytic amounts of hexacyano-ironS(III) acid or $Na_2(Fe(CN)_5NO)$ with cooling by solid carbon dioxide. These complex compounds are used to catalyze the hydration of olefins and suppress polymerization.

We have now found that cyclohexanol can be produced continuously and in excellent yields from cyclohexene in two stages involving the addition of sulfuric acid followed by hydration, provided that the addition of sulfuric acid is carried out in the presence of iron(II) sulfate. In this continuous process for the manufacture of cyclohexanol by indirect hydration of cyclohexene, it is convenient to operate the first stage at atmospheric pressure using a hot sulfuric acid saturated with $Fe_2SO_4$, by which means the cyclohexene is converted to the corresponding cyclohexyl sulfate, which is hydrolyzed in the second stage with cyclohexanol-saturated water to form cyclohexanol.

The concentration of sulfuric acid in the first stage may generally be between 50 and 70 % and we prefer to use a 60% solution. The amount of sulfuric acid used may be from 0.8 to 5 moles and advantageously from 1.5 to 2 moles per mole of cyclohexene. In a preferred embodiment of the process, the sulfuric acid is added to the cyclohexene. The temperature of the reaction solution may be from 50° to 100° C and we prefer to work at the boiling temperature of cyclohexene (82°–83° C). The addition of iron(II) sulfate serves the purpose of preventing the occurrence of undesirable side reactions which would reduce the yield. The iron-(II) sulfate may be added in amounts up to its saturation point in the sulfuric acid or sulfuric acid solution used for the addition process.

The concentration of sulfuric in the second stage is advantageously lower than in the first stage. For example, it may be 40% and it is preferred to use a sulfuric acid concentration of 30% for the hydrolysis of cyclohexyl sulfate. In the process of the invention, the yield of cyclohexanol is more than 95% by weight for a cyclohexene conversion of 60%.

The process of the invention may be carried out by passing cyclohexene through line 6 to the reactor 1, where it is caused to boil and the temperature is maintained at 82° C by vapor cooling while a 60% sulfuric acid solution, heated at 110° C, is fed to the reactor through line 7 and thus added to the boiling cyclohexene. The sulfuric acid leaving the reactor is diluted with water to a concentration of 30% in a mixing line 8 and passes to a saponifying and stripping column 2 operating at atmospheric temperature and a temperature of 110° C. The concentrated sulfuric acid (60%) which collects at the base of this column is recycled to the absorption reactor 1 through line 9. The overheads leaving the stripping column 2 consist of cyclohexene, cyclohexanol and water. The said cyclohexanol forms an azeotrope with water in the proportions 20:80 by weight, which boils at 97° C. The overheads pass to a separator 3 operating at 20° C and in which an aqueous phase containing 3% of cyclohexanol, which is used for the hydrolysis of the alkyl sulfate, and an organic phase comprising cyclohexene, cyclohexanol and traces of water are obtained. The organic phase is fed to a column 4 for the removal of cyclohexene and traces of water. Residual water is removed by adding cyclohexene at the top of the column. In a second column 5, cyclohexanol is removed from the residue. The process is illustrated in the accompanying drawing in the form of a flow diagram.

EXAMPLE 325 g of 60% sulfuric acid, heated at 110° C and containing 3 g of iron(II) sulfate dissolved therein, are added to 82 g of boiling cyclohexene over 30 minutes. The reaction solution is heated at 80° C for a further 30 minutes and then diluted to a sulfuric acid concentration of 30% with cyclohexanol-saturated water. The mixture is then distilled to give 52 g of cyclohexanol and 37 g of cyclohexene, equivalent to a conversion of 55% at a cyclohexanol yield of 95%.

We claim:

1. In a method for the continuous production of cyclohexanol from cyclohexene in two stages involving the addition of sulfuric acid and hydration, the improvement which comprises mixing sufficient sulfuric acid with said cyclohexene to provide a sulfuric acid concentration in the first stage of from 50 to 70% by weight in the presence of iron(II) sulfate while the temperature of the reaction solution is kept at from 50° to 100° C.

2. A method as set forth in claim 1 in which the temperature of the reaction solution is maintained at the boiling temperature of cyclohexene at atmospheric pressure while adding said sulfuric acid.

3. A method as set forth in claim 1 in which from 0.8 to 5 moles of sulfuric acid is added per mole of cyclohexene.

* * * * *